(12) United States Patent
Smayda

(10) Patent No.: US 10,448,672 B2
(45) Date of Patent: Oct. 22, 2019

(54) VAPORIZER HAVING INDUCTION HEATING AND METHODS OF USING SAME

(71) Applicant: Richard Smayda, Nazareth, PA (US)

(72) Inventor: Richard Smayda, Nazareth, PA (US)

( * ) Notice: Subject to any disclaimer, the term of this patent is extended or adjusted under 35 U.S.C. 154(b) by 0 days.

(21) Appl. No.: 16/016,367

(22) Filed: Jun. 22, 2018

(65) Prior Publication Data

US 2018/0295890 A1    Oct. 18, 2018

Related U.S. Application Data

(63) Continuation-in-part of application No. 15/429,209, filed on Feb. 10, 2017, now Pat. No. 10,004,273.

(51) Int. Cl.

| | |
|---|---|
| *A24F 47/00* | (2006.01) |
| *G07C 9/00* | (2006.01) |
| *H05B 6/10* | (2006.01) |
| *G01N 21/3577* | (2014.01) |
| *H05B 6/06* | (2006.01) |
| *G01N 21/35* | (2014.01) |

(52) U.S. Cl.
CPC ....... *A24F 47/008* (2013.01); *G01N 21/3577* (2013.01); *G07C 9/00563* (2013.01); *H05B 6/06* (2013.01); *H05B 6/108* (2013.01); *G01N 21/35* (2013.01)

(58) Field of Classification Search
None
See application file for complete search history.

(56) References Cited

U.S. PATENT DOCUMENTS

2010/0028978 A1*  2/2010  Angros ............... B01L 3/0293
                                                            435/283.1
2016/0325055 A1* 11/2016  Cameron ............. A61M 11/005

* cited by examiner

*Primary Examiner* — Michael J Felton
(74) *Attorney, Agent, or Firm* — James R. McDaniel

(57) ABSTRACT

A vaporizer, including a removable panel; and a main body assembly such that the removable panel is removably attached to the main body assembly, wherein the main body assembly is further comprised of; a crucible/pan assembly such that a material to be vaporized is located within the crucible/pan assembly, an induction heater such that the induction heater is located adjacent to the crucible/pan assembly for induction heating of the crucible/pan assembly which in turn vaporizes the material to be vaporized located within the crucible/pan assembly, a removable battery assembly located adjacent to the induction heater, an electronics assembly operatively connected to the battery and the induction heater, and an interchangeable mouthpiece assembly operatively attached to the crucible/pan assembly for allowing vapors from the material to be vaporized to be inhaled by an end user.

15 Claims, 3 Drawing Sheets

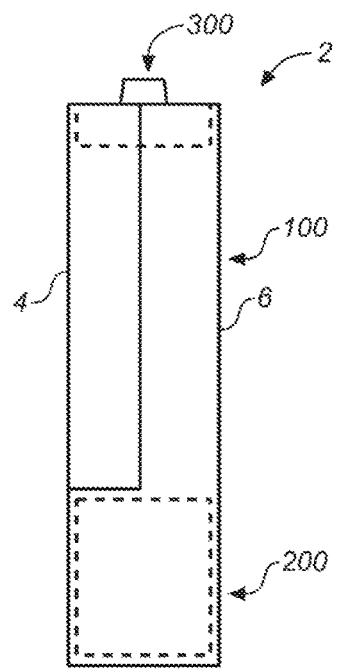
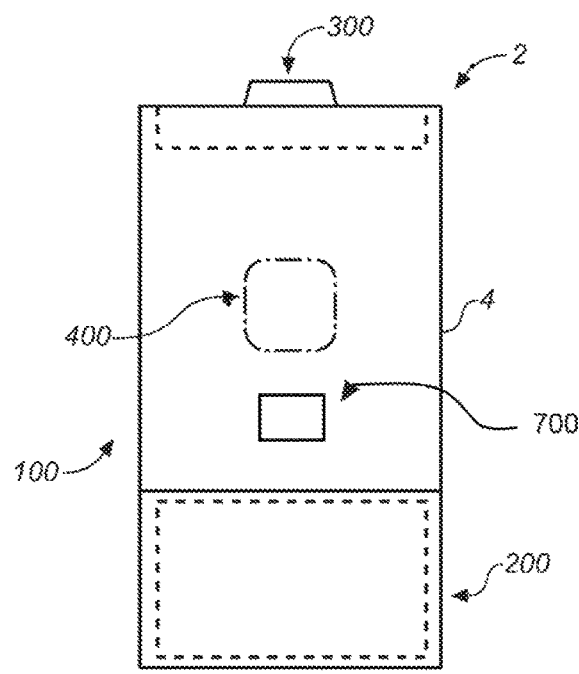
FIG. 1     FIG. 2
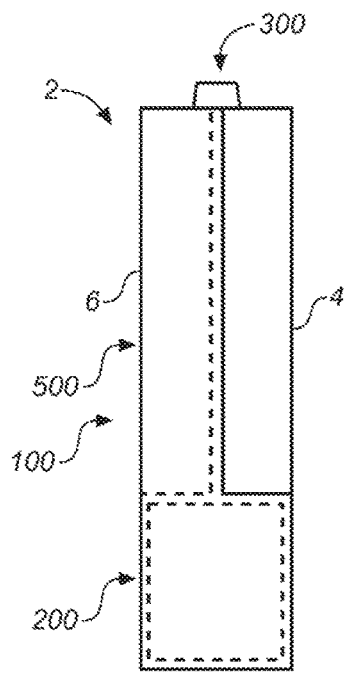
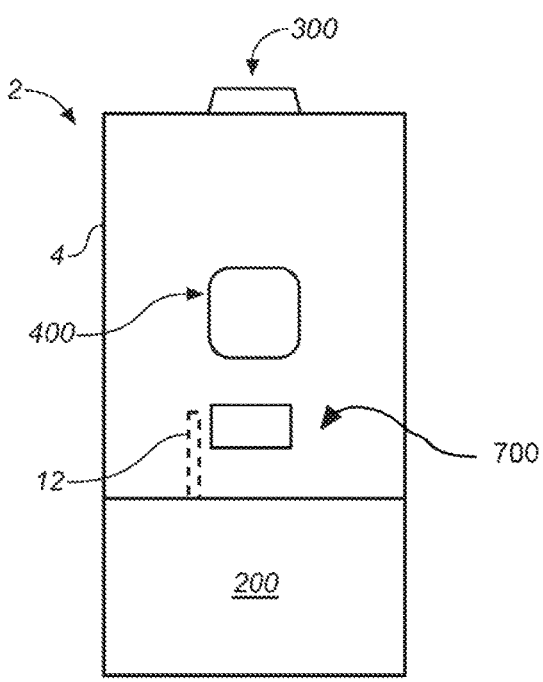
FIG. 3     FIG. 4

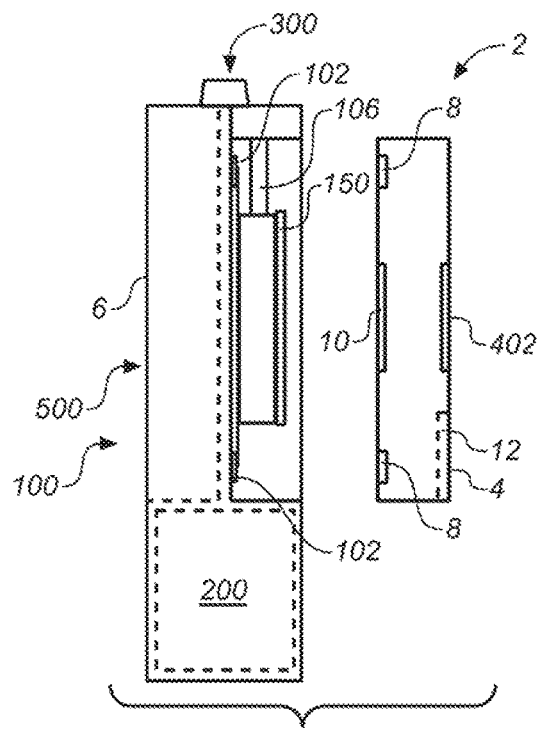
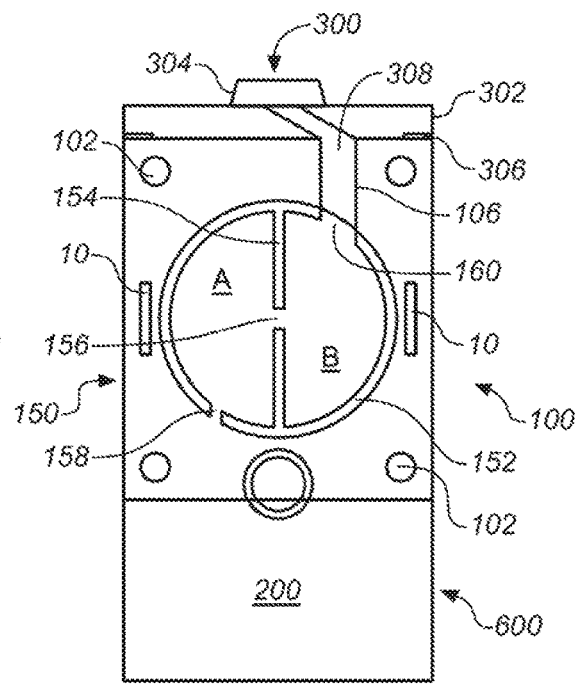
FIG. 5    FIG. 6
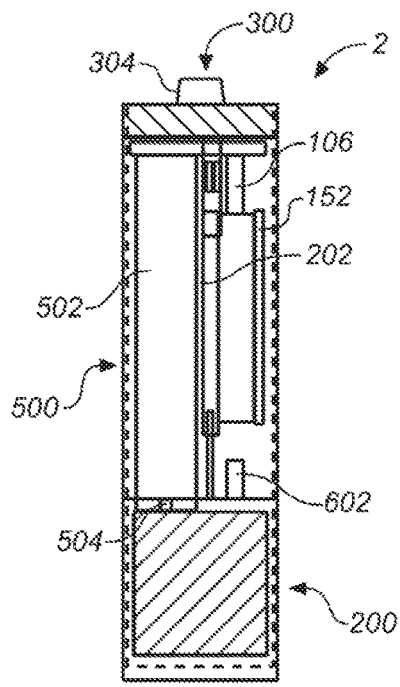
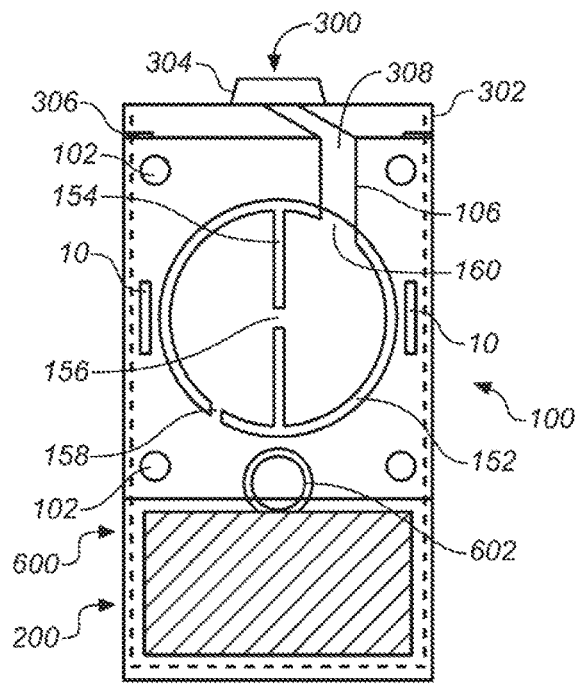
FIG. 8    FIG. 7

VAPORIZER HAVING INDUCTION HEATING AND METHODS OF USING SAME

CROSS-REFERENCE TO RELATED APPLICATION

This application is a continuation-in-part of U.S. patent application Ser. No. 15/429,209, filed on Feb. 10, 2017, the disclosure of which is hereby incorporated by reference in its entirety to provide continuity of disclosure to the extent such disclosures are not inconsistent with the disclosure herein.

FIELD OF THE INVENTION

The present invention is generally related to a hand-held vaporizer that uses induction heating in order to more quickly and efficiently heat up the material that is to be vaporized. The hand-held vaporizer also includes a biometric locking mechanism, interchangeable mouthpieces, a hot-swap, chargeable battery source, and a molecular sensor.

BACKGROUND OF THE INVENTION

Prior to the present invention, as set forth in general terms above and more specifically below, it is known, to employ various types of vaporizers. While these various vaporizers may have been, generally satisfactory, the currently available vaporizers suffer from several well-known deficiencies. For example, the current vaporizers are relatively expensive, not very robust in their design, require that the vaporizer be taken apart in order to remove and replace the battery, cannot be locked or otherwise secured to prevent unauthorized use of the vaporizer, do not include interchangeable mouthpieces, and do not include a molecular sensor that will allow the user to determine the chemical, biological and/or physical composition of the material that the user desires to vaporize. Therefore, there is a need in the vaporizer art for a new and improved hand-held vaporizer that uses induction heating in order to more quickly and efficiently heat up the material that is to be vaporized, wherein the hand-held vaporizer also includes a biometric locking mechanism, interchangeable mouthpieces, an external battery source, and a molecular sensor.

It is a purpose of this invention to fulfill these and other needs in the vaporizer art in a manner more apparent to the skilled artisan once given the following disclosure.

BRIEF SUMMARY OF THE INVENTION

A first aspect of the present invention is a handheld vaporizer, including a removable panel, and a main body assembly such that the removable panel is removably attached to the main body assembly, wherein the main body assembly is further comprised of; a crucible/pan assembly having a first side and a second side such that a material to be vaporized is located within the first side of the crucible/pan assembly, wherein the crucible/pan assembly further includes a crucible/pan having a plurality of chambers, wherein the crucible/pan is further comprised of a core such that the core is constructed of cast iron, and a layer of a glass material that surrounds the core, a divider located on the crucible/pan such that the plurality of chambers is divided by the divider, an opening located within the divider, and an opening located on each of the plurality of chambers, an induction heater having a first side and a second side such that the first side of the induction heater is located adjacent to the second side of the crucible/pan assembly for induction heating of the crucible/pan assembly which in turn vaporizes the material to be vaporized located within the first side of the crucible/pan assembly, a removable battery assembly located adjacent to the second side of the induction heater, an electronics assembly operatively connected to the battery and the induction heater, and an interchangeable mouthpiece assembly operatively attached to the crucible/pan assembly for allowing vapors from the material to be vaporized to be inhaled by an end user.

In one embodiment of the first aspect of the present invention, the removable panel includes a plurality of first magnets operatively attached around a periphery of the removable panel.

In another embodiment of the first aspect of the present invention, the main body assembly includes a plurality of second magnets located around of periphery of the main body assembly such that the plurality of second magnets interact with the plurality of first magnets in order to assist in attaching the removable panel to the main body assembly.

In another embodiment of the first aspect of the present invention, the removable panel includes a biometric sensor attached to the removable panel and operatively connected to the electronics assembly, and a plurality of locks attached to the removable panel and operatively connected to the biometric sensor.

In still another embodiment of the first aspect of the present invention, the interchangeable mouthpiece assembly includes a mouthpiece base having a first end and a second end, a mouthpiece operatively attached to the first end of the mouthpiece base, at least mouthpiece magnet operatively connected to the second end of the mouthpiece base for removably attaching the mouthpiece base to the main body assembly, and a mouthpiece, opening located in the mouthpiece base that operatively connects the mouthpiece to the crucible/pan assembly.

In still yet another embodiment of the first aspect of the present invention, the removable battery assembly includes a battery, and an electrical connector operatively connected to the battery and the electronics assembly.

In an even further embodiment of the first aspect of the present invention, the molecular sensor assembly further includes an infrared spectrometer.

In a further embodiment of the first aspect of the present invention, the hand-held vaporizer further includes a display screen operatively connected to the removable panel.

A second aspect of the present invention is a vaporizer having induction heating, including a removable panel, and a main body assembly such that the removable panel is removably attached to the main body assembly, wherein the main body assembly is further comprised of; a crucible/pan assembly having a first side and a second side such that a material to be vaporized is located within the first side of the crucible/pan assembly, wherein the crucible/pan assembly further includes a crucible/pan having a plurality of chambers, wherein the crucible/pan is further comprised of a core such that the core is constructed of cast iron, and a layer of a glass material that surrounds the core, a divider located on the crucible/pan such that the plurality of chambers is divided by the divider, an opening located within the divider, and an opening located on each of the plurality of chambers, an induction heater having a first side and a second side such that the first side of the induction heater is located adjacent to the second side of the crucible/pan assembly for induction heating of the crucible/pan assembly which in turn vaporizes the material to be vaporized located within the first side of the crucible/pan assembly, a removable battery assembly located adjacent to the second side of the induction heater, an electronics assembly operatively connected to the battery and the induction heater, and an interchangeable mouthpiece assembly operatively attached to the crucible/pan assembly for allowing vapors from the material to be vaporized to be inhaled by an end user.

In one embodiment of the second aspect of the present invention, the removable panel includes a plurality of first magnets operatively attached around a periphery of the removable panel.

In another embodiment of the second aspect of the present invention, the main body assembly includes a plurality of second magnets located around of periphery of the main body assembly such that the plurality of second magnets interact with the plurality of first magnets in order to assist in attaching the removable panel to the main body assembly.

In another embodiment of the second aspect of the present invention, the removable panel includes a biometric sensor attached to the removable panel and operatively connected to the electronics assembly, and a plurality of locks attached to the removable panel and operatively connected to the biometric sensor.

In still another embodiment of the second aspect of the present invention, the interchangeable mouthpiece assembly includes a mouthpiece base having a first end and a second end, a mouthpiece operatively attached to the first end of the mouthpiece base, at least mouthpiece magnet operatively connected to the second end of the mouthpiece base for removably attaching the mouthpiece base to the main body assembly, and a mouthpiece opening located in the mouthpiece base that operatively connects the mouthpiece to the crucible/pan assembly.

In an even further embodiment of the second aspect of the present invention, the molecular sensor assembly further includes an infrared spectrometer.

In a further embodiment of the second aspect of the present invention, the hand-held vaporizer further includes a display screen operatively connected to the removable panel.

A third aspect of the present invention is a method of using a hand-held vaporizer, including the steps of; removing a removable panel from a main body of a hand-held vaporizer, inserting a desired amount of a material to be vaporized into a crucible/pan assembly, wherein the crucible/pan assembly further includes a crucible/pan having a plurality of chambers, wherein the crucible/pan is further comprised of a core such that the core is constructed of cast iron, and a layer of a glass material that surrounds the core, a divider located on the crucible/pan such that the plurality of chambers is divided by the divider, an opening located within the divider, and an opening located on each of the plurality of chambers, attaching the removable panel back onto the main body of the hand-held vaporizer, activating an induction heater that is located adjacent to the crucible/pan assembly, induction heating the crucible/pan assembly so as to vaporize the material that is to be vaporized, transporting a vapor from the vaporized material to an interchangeable mouthpiece assembly, and inhaling, by an end user, the vapor from the vaporized material through the interchangeable mouthpiece assembly.

In another embodiment of the third aspect of the present invention, the method further includes the step of providing the removable panel with a biometric sensor and a plurality of locks such that the biometric sensor operates in conjunction with the plurality of locks located on the removable panel in order to prevent unauthorized use of the hand-held vaporizer.

In a further another embodiment of the third aspect of the present invention, the step of using a molecular sensor further includes the step of using an infrared spectrometer to determine a chemical, biological and/or physical composition of the material to be vaporized prior to the material being vaporized.

In a yet another embodiment of the third aspect of the present invention, the step of providing the removable panel further includes the step of providing a display screen on the removable panel.

The preferred hand-held vaporizer having induction heating, according to various embodiments of the present invention, offers the following advantages: ease of use; lightness in weight; durability; excellent heating characteristics: the ability to prevent unauthorized use of the vaporizer; the use of interchangeable mouthpieces; the use of an external battery; the use of a molecular sensor; portability; and reduced cost. In fact, in many of the preferred embodiments, these advantages are optimized to an extent that is considerably higher than heretofore achieved in prior, known vaporizers.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which:

FIG. 1 is a schematic, side view of a hand-held vaporizer, constructed according to the present invention;

FIG. 2 is a schematic, front view of the hand-held vaporizer of FIG. 1, constructed according to the present invention;

FIG. 3 is a schematic, side view of the hand-held vaporizer with the lid attached, constructed according to the present invention;

FIG. 4 is a schematic, front view of the hand-held vaporizer with the lid attached, constructed according to the present invention;

FIG. 5 is a schematic, side view of the hand-held vaporizer with the lid removed, according to the present invention;

FIG. 6 is a schematic, front view of the hand-held vaporizer with the lid removed, according to the present invention;

FIG. 7 is a detailed, front view illustration of the hand-held vaporizer with the lid removed, according to the present invention;

FIG. 8 is a detailed, side view illustration of the hand-held vaporizer with the lid removed, according to the present invention:

DETAILED DESCRIPTION OF THE PREFERRED EMBODIMENTS OF THE INVENTION

Figure 9:
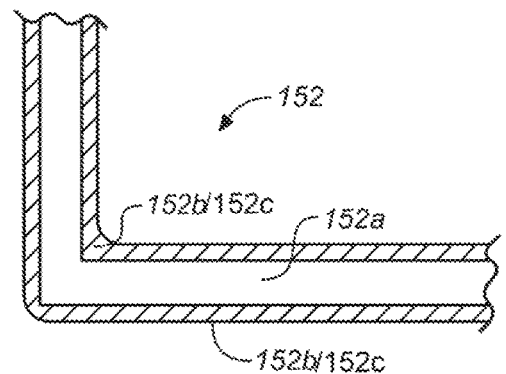
FIG. 9 is a cross-sectional view of the crucible assembly of the hand-held vaporizer, constructed according the present invention.

In order to address the previously discussed shortcomings of the known vaporizers, reference is made now to FIG. 1, where there is illustrated hand-held vaporizer 2 having induction heating. As will be explained hereinafter in greater detail, the hand-held vaporizer 2 utilizes induction heating in order to more quickly and efficiently heat up the materials, such as tobacco, coffee, alcohol, dry herbs, botanicals, essential oils, e-liquids, wax products or the like to be inhaled or otherwise consumed by the end user. As will be also discussed in greater detail later, the hand-held vaporizer 2 also includes a biometric locking mechanism, interchangeable mouthpieces, an external battery source, and a molecular sensor. However, it is to be understood that hand-held vaporizer 2 can also be constructed to be a desk-top unit and still utilize the unique aspects of the present invention.

As shown in FIG. 1, there is illustrated a unique hand-held vaporizer 2 which includes a removable panel 4, a vaporizer main body assembly 100 having outer shell 6 and electronics assembly 200 (located within main body assembly 100), a replaceable mouthpiece assembly 300, and a display device 700.

With respect to removable panel 4, panel 4 and outer shell 6, preferably are constructed of any suitable, lightweight material that is durable, impact resistant, and temperature resistant, such as titanium or the like. As will be discussed in greater detail later, removable panel 4 is attached to main body assembly 100 by a unique locking mechanism.

With respect to FIG. 2, there is illustrated biometric sensor assembly/on-off 400 which is attached to removable panel 4. As will be discussed in greater detail later, biometric sensor/on-off assembly 400 is provided on the hand-held vaporizer 2 in order to prevent an unauthorized use of hand-held vaporizer 2. The unique components and aspects of the present invention will now be discussed in relation to the various components and assemblies of the hand-held vaporizer 2.

Hand-Held Vaporizer Components and Assemblies

Hand-Held Vaporizer Overall Assembly

With respect to FIG. 3, there is illustrated the overall assembly of hand-held vaporizer 2. As discussed earlier, hand-held vaporizer 2 includes a removable panel 4 which is removable along the direction of arrow (X), a vaporizer main body assembly 100 having outer shell 6, electronics assembly 200, and a replaceable mouthpiece assembly 300.

As shown in FIG. 4, there is illustrated a front view of the overall assembly of hand-held vaporizer 2. As discussed earlier, biometric sensor assembly/on-off 400 is located on removable panel 4. As will be discussed in greater detail later, biometric sensor assembly/on-off 400 is provided on the hand-held vaporizer 2 in order to prevent an unauthorized use of hand-held vaporizer 2.

Hand-Held Vaporizer Panel Assembly and Panel Locking Assembly

Regarding FIG. 5, as shown in FIG. 5, removable panel 4 has been removed from main body assembly 100. As shown in FIG. 5, removable panel 4 includes magnets 8, panel locks 10 and biometric sensor assembly/on-off 400. Magnets 8 are located around a periphery of removable panel 4 in order to retain removable panel 4 onto main body assembly 100. Preferably, magnets 8 are constructed of any suitable, durable magnetic material that is capable of properly retaining removable panel 4 on main body assembly 100. It is to be understood that magnets 8 interact with magnets 102 on main body assembly 100, as will be discussed in greater detail later.

With respect to panel locks 10 and biometric sensor assembly/on-off 400, panel locks 10 are any suitable, durable locks that can be used in conjunction with biometric sensor assembly/on-off 400 in order to prevent the unauthorized use of hand-held vaporizer 2. Preferably, panel locks 10 are constructed of a magnetic material that is capable of attaching itself to main body assembly 100.

As will be discussed in greater detail later, biometric sensor assembly/on-off 400 includes a conventional biometric sensor/on-off button 402 located on the front of removable panel 4. The biometric sensor/on-off button 402 is then conventionally attached to the panel locks 10 and the electronics assembly 200. In this manner, the end user simply scans his/her index finger over the biometric sensor/on-off button 402, for example, so that the end user's index fingerprint is conventionally scanned by the biometric sensor/on-off button 402. The end user's unique fingerprint is then conventionally stored in the end users smartphone, laptop, tablet or other similar electronic device (not shown). If the end user wants to use the hand-held vaporizer 2, the end user then merely scans his/her index finger over the biometric sensor/on-off button 402. If the fingerprint is recognized by the smartphone, laptop, tablet or other similar electronic device (not shown), the smartphone, laptop, tablet or other similar electronic device (not shown) conventionally sends a signal to the panel locks 10 to disengage panel locks 10 from main body assembly 100. The end user can then remove panel 4 from main body assembly 100, as previously discussed.

As another unique aspect of the present invention, the biometric sensor/on-off button 402 can be used to conventionally power on/activate induction heating coil 202 and to power off/de-activate induction heating coil 202. In this manner, biometric sensor/on-off button 402 is conventionally connected to electronics assembly 200 and, in particular, induction heating coil 202. As will be described in greater detail later, the end user simply presses or otherwise activates biometric sensor/on-off button 402 in order to turn on induction heating coil 202 so that the material to be vaporized that is located in crucible 150 is vaporized. Once the material to be vaporized has been completely vaporized, the end user conventionally presses biometric sensor/on-off button 402 in order to turn off induction heating coil 202.

Located on removable panel 4 is a groove or channel that acts as an air intake groove or channel 12. Preferably, air intake groove or channel 12 is constructed in removable panel 4 by conventional techniques such as grinding, etching, cutting, milling or the like. As will described in greater detail later, when the removable panel 4 is attached to shell 6, one end of air intake groove or channel 12 is located adjacent to one end of the crucible assembly 150 (near crucible chamber (A)). The other end of groove or channel 12 is located at or near the bottom edge of removable panel 4 so that this end of air intake groove or channel can receive fresh air that is able to get between the bottom of removable panel 4 and the edge of shell 6 where removable panel 4 contacts shell 6. The fresh air is then transported along air intake groove of channel 12 into crucible 152 through air intake pipe opening 158.

Hand-Held Vaporizer Main Body Assembly

Also, shown in FIG. 5 is the inside of main body assembly 100 after removable panel 4 has been removed. With respect to main body assembly 100, main body assembly 100 includes, in part, magnets 102, vapor pipe 106, crucible assembly 150, electronics assembly 200 and mouthpiece assembly 300. Regarding magnets 102, preferably, magnets 102 are conventionally attached to main body assembly 100. Also, magnets 102, preferably, are constructed of the same material as magnets 8.

Located at the top end of crucible assembly is vapor pipe 106. Vapor pipe 108 is located adjacent one end to the crucible assembly 150. The other end of air intake pipe 104 is located adjacent to the bottom of mouthpiece assembly 300. Preferably, vapor pipe 106 is constructed of any suitable durable, impact resistant, and temperature resistant metallic material such as titanium, ceramic, glass, Pyrex® or the like.

Crucible/Pan Assembly

Figure 10:
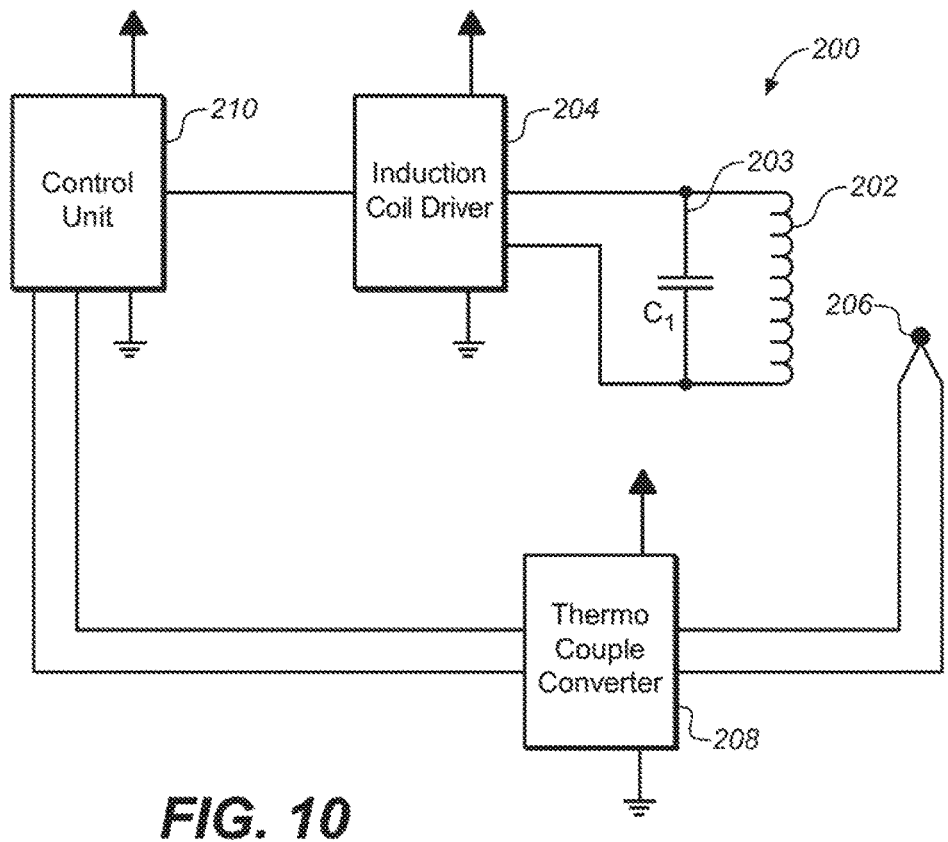
FIG. 10 is a schematic illustration of the electronics assembly of the hand-held vaporizer, constructed according the present invention.

With respect to crucible assembly 150, as shown more clearly in FIGS. 6 and 9, crucible assembly includes, in part, crucible/pan 152, crucible divider 154, divider opening 156, air intake pipe opening 158, and vapor pipe opening 160. Regarding crucible/pan 152, one of the unique aspects of the present invention is the construction of the crucible/pan 152. As shown more clearly in FIG. 9, crucible/pan 152 has a core 152a which is surrounded by a ceramic layer 152b. Preferably, crucible core 152a is constructed of any suitable, durable, heat conductive material such as cast iron. Preferably, ceramic layer 152b is constructed of any suitable, durable, heat conductive material such as a titanium ceramic including, but not limited to titanium diboride ($TiB_2$). As will be described in greater detail later, the unique aspect of the crucible/pan 152 is that crucible/pan 152 can be easily and quickly heated by induction heating coil 202, as shown in FIGS. 8 and 10. Furthermore, once the induction heating coil 202 has been turned off, crucible/pan 152 quickly and easily cools down so that the end user can remove the used material that was vaporized and add more material to be vaporized, if desired by the end user.

It is to be understood that instead of using the ceramic layer 152b, a glass coating or housing 152c can be used. In particular, the glass coating or housing 152c can be conventionally applied to the outside of crucible core 152a. In this manner, the ceramic layer 152b does not have to be applied to the outside of crucible core 152a. It is to be understood that the glass coating or housing 152c can be constructed of a suitable, durable, heat conductive glass material.

Regarding the crucible divider 154, crucible divider 154 is attached to crucible 152 by conventional techniques. Also, crucible divider 154 includes the same materials as crucible/pan 152 which allows crucible/pan 152 to easily and quickly heat up and cool down. An opening 156 is conventionally formed in crucible divider 154 in order to allow the air and/or the vapor from the vaporized material to flow from crucible chamber (A) to crucible chamber (B), as will be discussed in greater detail later.

Located at the bottom of crucible chamber (A) is air intake pipe opening 158. Air intake pipe opening 158 is conventionally formed in crucible/pan 152. As shown in FIG. 6, air intake pipe opening 158 allows air intake pipe 104 to interact with crucible/pan 152 in order to provide air to crucible/pan 152 at chamber (A).

Located, at the top of crucible chamber (B) is vapor pipe opening 160. Vapor pipe opening 160 is conventionally formed in crucible/pan 152. As shown in FIG. 6, vapor pipe opening 160 allows vapor pipe 106 to interact with crucible/pan 152 in order to transport the vapor from the vaporized material that has been induction heated in crucible/pan 152 to the mouthpiece assemble 300 so that the vapor from the vaporized material can be inhaled or otherwise consumed by the end user.

Locking Assembly

Regarding the magnets 102, as shown more clearly in FIG. 6, there are preferably four (4) magnets located on main body assembly 100 in order to retain removable panel 4 (FIG. 5) on main body assembly 100. Preferably, magnets 102 are located around a periphery of the main body assembly 100 in order to properly retain removable panel 4 (FIG. 5) on main body assembly 100. As discussed earlier, magnets 102 interact with magnets 8 located on the periphery of removable panel 4.

Regarding panel locks 10, as shown more clearly in FIG. 6, there are two (2) panel locks 10 located on main body assembly 100 in order to secure/lock removable panel 4 (FIG. 5) to main body assembly 100. Preferably, panel locks 10 are located on both sides of crucible/pan 152 of the main body assembly 100 in order to properly secure/lock removable panel 4 (FIG. 5) to main body assembly 100 through the use of the biometric sensor assembly/on-off 400.

Interchangeable Mouthpiece Assembly

With respect to mouthpiece assembly 300, as shown in FIG. 6 and as described in greater detail later, mouthpiece assembly 300 includes, in part, mouthpiece base 302, mouthpiece 304, mouthpiece assembly magnets 306 and mouthpiece opening 308. Mouthpiece base 302, preferably, is constructed so that fits over crucible/pan 152 and mouthpiece opening 308 aligns with the other end of vapor pipe 106. Preferably, mouthpiece base 302 is constructed of any suitable durable, impact resistant, and temperature resistant metallic material, ceramics, thermoplastic polymeric materials such as polyether ether ketone (PEEK) or the like.

Located on the bottom of mouthpiece base 302 are mouthpiece assembly magnets 306. Preferably, mouthpiece magnets 306 are constructed of a magnetic material that is capable of removably attaching mouthpiece base 302 to main body assembly 100.

Mouthpiece 304 is located on top of mouthpiece base 302. It is to be understood that mouthpiece 304 can be formed integrally with mouthpiece base 302 or it can be conventionally attached to the top of mouthpiece base 302.

Another unique aspect of the present invention is this particular mouthpiece assembly 300. As shown in FIG. 6, mouthpiece assembly is removably attached to main body assembly 100 by mouthpiece assembly magnets 306. A variety of different mouthpieces 304 can be used with hand-held vaporizer 2. The end user merely has to select the mouthpiece assembly 300 that has the desired mouthpiece 304 and attach the desired mouthpiece assembly 300 to the main body assembly 100 through the use of the mouthpiece magnets 306. If the end user desires to utilize a different mouthpiece assembly 300, the end user simply removes the mouthpiece assembly 300 that is currently located on the hand-held vaporizer 2 and attach the desired mouthpiece assembly 300.

Molecular Sensor Assembly

With respect to FIG. 7, there is illustrated in greater detail hand-held vaporizer 2 which also includes molecular sensor assembly 600. Molecular sensor assembly 600 includes infrared spectrometer 602 which is conventionally retained on main body assembly 100. Also, infrared spectrometer 602 is conventionally attached to electronics assembly 200. It is to be understood that infrared spectrometer 602 is used to analyze the interaction of infrared light with a molecule. This interaction can be analyzed in three ways by measuring absorption, emission and reflection of the infrared light as it interacts with the molecule.

A further unique aspect of the present invention involves the use of molecular sensor assembly 600. It is known that molecular sensors are devices that detect, record, and indicate a physical, biological or chemical property. Typically, the molecular sensor includes three (3) main elements, namely, a detector for capturing and recognizing the scanned material, a transducer for signal transduction, and a signal processor for processing the signal from the signal transducer. As an example, the molecular sensor (e.g., the infrared spectrometer 602 in the present invention) can convert a biological, chemical or physical quantity of a material into a detectable signal, such as an electrical signal. Through the use of the transducer and the signal processor, the molecular sensor (e.g., the infrared spectrometer 602 in the present invention) is able to provide information to the end user as to the chemical, biological or physical nature of the material that was scanned.

For a more real-life example, suppose the end user desires to vaporize a particular type of tobacco grown in Turkey. The end user goes to his/her favorite tobacco shop to see if the tobacco shop carries the desired type of tobacco. The end user is informed by the clerk at the tobacco shop that such a desired type of tobacco is available for sale at the tobacco shop. However, prior to purchasing the desired type of tobacco, the end user, through the use of the molecular sensor assembly 600 (e.g., the infrared spectrometer 602 in the present invention), is able to scan the tobacco, obtain a measurement of the biological, chemical, and physical properties of the tobacco being offered for sale by the tobacco shop and make a determination based upon information from the molecular sensor assembly 600 (e.g., the infrared spectrometer 602 in the present invention) that indeed the tobacco being offered by the tobacco shop is from Turkey.

As, a further example of how the end user is informed as to the chemical, biological and/or physical composition of the tobacco that is being offered for sale by the tobacco shop, the molecular sensor assembly 600 can conventionally interact with the end user's smartphone, laptop, tablet or other similar electronic device (not shown). In this manner, the molecular sensor assembly 600, through the electronics assembly 200, interacts with the end user's smartphone, laptop, tablet or other similar electronic device via a conventional wireless local networking technology such as Bluetooth® or Wi-Fi. The end user scans the material to be vaporized by the molecular sensor assembly 600 (e.g., the infrared spectrometer 602 in the present invention) and the scanned information is forwarded through the wireless local network (not shown) to a conventional server database (not shown). A listing of the chemical, biological and/or physical properties of a variety of materials that are known to be used in vaporizers is conventionally stored in the database. The chemical, biological and/or physical properties of the scanned material to be vaporized are conventionally compared to those chemical, biological, and/or physical properties of the known materials stored in the database. If a match is found between the chemical, biological and/or physical properties of the scanned material to be vaporized and the chemical, biological, and/or physical properties of the known materials stored in the database, the end user is conventionally informed of the result. For example, if the end user scans a material that he believes to be Turkish tobacco and the database sends a text message to the end user's smartphone that the scanned material is most likely Russian tobacco, the end user will now be apprised as to the actual origin of the tobacco. Furthermore, the end user can also inform the tobacco shop as to the real origin of the tobacco (Russia, not Turkey).

Electrical Assembly

Regarding electrical assembly 200, as shown more clearly in FIGS. 7 and 10, electrical assembly 200, includes, in part, induction heating coil 202, capacitor 203, induction coil driver 204, thermocouple 206, thermocouple converter 208, and control unit 210.

With respect to inductor heating coil 202, induction heating coil 202 is conventionally constructed of copper wire wound into a coil so that the induction heating coil 202 will inductively heat crucible/pan 152, as will be discussed in greater detail later. Capacitor 203 is conventionally used with induction heating coil 202 to form a resonant tank circuit that has a frequency of approximately 200 kHz. A conventional induction coil driver 204 powers the induction heating coil 202 such that the coil driver operates at a voltage of 12 volts (direct current) at 1-6 amps. A conventional control unit 210 is used to control the induction coil driver 204 and conventional thermocouple converter 208. In this manner, a conventional thermocouple 206, which is located adjacent to the induction heating coil 202, is used to take readings of the induction heating coil 202. Once a desired temperature of the induction heating coil 202 is reached, thermocouple 206, through thermocouple converter 208 and control unit 210, is used to turn off (or turn on, if needed), power to the induction heating coil 202.

An even further unique aspect of the present invention involves the induction heating of the crucible/pan 152 by induction heating coil 202. The use of the induction heating coil 202 (which is located behind crucible/pan 152 as shown in FIG. 8) allows crucible/pan 152 to be easily and quickly heated to very high temperatures (≥400° F. and possibly up to 800° F.). The current vaporizers are simply not able to heat the material to be vaporized to such high temperatures. This is because the current models use conduction heaters that utilize resistive metal which heats when a current is applied. These current heating systems are only able to heat the material to be vaporized to 150-480° F. Also, since the current vaporizers are only able to heat the material to be vaporized to 150-480° F., quite often there is noticeable, unvaporized material left in the crucible of the current vaporizers. The higher temperature range of the present invention significantly reduces the amount of unvaporized material left in the crucible of the present invention. Also, the higher temperature range of the present invention significantly reduces the amount of ash or other residue left in the crucible/pan 152 of the present invention since substantially all of the material placed within the crucible/pan 152 should be vaporized at the higher temperatures produced by the present invention.

As discussed above, another unique aspect of the induction heating coil 202 and crucible/pan 152 is that once the power is turned off to the induction heating coil 202, induction heating coil 202 and crucible/pan 152 begin to cool rapidly. Also, once power is turned off to induction heating coil 202, within a matter of seconds, the end user will be able to come into contact with induction heating coil 202 without being burned by induction heating coil 202. In this manner, the end user can quickly and easily, remove removable panel 4 from hand-held vaporizer 2, empty the residue from crucible/pan 152, add material to be vaporized to crucible/pan 152 and re-attach removable panel 4 to main body assembly 100.

Battery Assembly

With respect to FIGS. 5 and 8, battery assembly 500 is illustrated. As more clearly shown in FIG. 8, battery assembly 500 includes a conventional battery 502 that is conventionally retained within main body assembly 100 and conventionally attached to electrical assembly 200 by electrical connector 504. Preferably, battery 502 is a conventional, rechargeable battery.

A still further unique aspect of the present invention involves the use of battery assembly 500. In known vaporizers that use batteries to power the vaporizer, if the batteries need to be replaced, the end user must disassemble the entire vaporizer in order to remove and replace/recharge the battery. This clearly is time consuming and inconvenient. The present invention significantly reduces the time taken to remove and replace the battery. In particular, the end user merely removes the mouthpiece assembly 300, removes the battery 502, inserts a new battery 502 and re-attaches the mouthpiece assembly 300. In this manner, the end user can charge several batteries 502 on a conventional charging station such as a charging pad. This allows the end user to somewhat continuously use the hand-held vaporizer 2 by easily and quickly hot swap out the used batteries 502 with new fully-charged batteries 502.

Display Screen

As shown in FIGS. 1 and 4, there is illustrated a display screen 700. Display screen 700, preferably, is any suitable display screen such as an LED screen that is used to provide information to the end user regarding the operation of the hand-held vaporizer 2. In particular, display screen 700 can be used to display the temperature of the crucible 152, the actual chemical, biological, and/or physical properties of the material to be vaporized, the amount of battery life left in the battery 502, a notification to the user that the biometric sensor assembly/on-off 400 has been activated, a notification to the user that the panel locks 10 have been locked/unlocked, or the like. In this manner, the display screen 700 can be used instead of having to connect the hand-held vaporizer 2 to a smartphone, laptop, tablet or other similar electronic device (not shown) especially if such an electronic device is not readily available. It is to be further understood that display screen 700 is conventionally connected to battery assembly 500 and electrical assembly 200 so that the display screen 700 can display information regarding the usage and operation of the device.

Operation of Hand-Held Vaporizer

With reference now to FIGS. 3-10, the operation and use of the hand-held vaporizer 2 will be discussed. Initially, if the end user desires to know the actual chemical, biological, and/or physical properties of the material to be vaporized, the end user scans the material to be vaporized through the use of molecular scanner assembly 600. As discussed above, molecular assembly 600 conventionally interacts with a conventional database and display screen 700 and/or the end user's smartphone, laptop, tablet or other similar electronic device (not shown) via a conventional wireless local network (not shown) in order to inform the end user as to the actual chemical, biological, and/or physical properties of the material to be vaporized. If the end user is satisfied as to the chemical, biological, and/or physical properties of the material to be vaporized, the end user can then proceed with inserting or otherwise loading the material to be vaporized into the crucible/pan 152 of hand-held vaporizer 2.

As shown in FIGS. 3 and 5, the end user removes removable pan 4. It is to be understood that if the hand-held vaporizer 4 includes biometric sensor assembly/on-off 400, the end user must scan his/her finger over the biometric scanner, as previously discussed, in order to unlock panel lock 10 from main body assembly 100 and remove panel 4 from main body assembly 100. As discussed above, the display screen 700 can be used to inform the end user that the hand-held vaporizer 4 has been unlocked/locked.

Once removable panel 4 has been removed from main body assembly 100, as best seen in FIGS. 6 and 7, the end user then places the desired amount of the material to be vaporized into crucible/pan 15. It is to be understood that another unique aspect of the present invention is the use of the dual chambers (A and B) of crucible/pan 152. As best seen in FIGS. 6 and 7, the end user can add a desired amount of material to chamber (A) and/or chamber (B). However, it is to be understood that the end user may decide to only add material to be vaporized to chamber (A) so that chamber (B) can be used to further cool down the vapor from the vaporized material before the vapor enters mouthpiece assembly 300 to be subsequently inhaled or otherwise ingested by the end user. Also, the end user may decide to place one type of material to be vaporized in chamber (A) and another type of material to be vaporized in chamber (B) to create a combination of vapors.

After the material to be vaporized has been loaded or otherwise inserted into crucible/pan 152, the end user re-attaches removable panel 4 so that removable panel 4 is now securely attached to main body assembly 100 through the use of magnets 10 and 102.

Once the removable panel 4 has been secured to main body assembly 100, the end user simply presses or otherwise activates biometric sensor/on-off button 402 in order to turn on induction heating coil 202 so that induction heating coil 202 begins to induction heat crucible/pan 152 and the material to be vaporized that is located in crucible 150 is vaporized. As discussed above, the display screen 700 can be used to inform the end user that the induction heating coil 202 has been activated.

Once it has been determined that all of the material to be vaporized that was inserted into crucible/pan 152 has been completely vaporized, the end user can then conventionally press biometric sensor/on-off button 402 in order to turn off induction heating coil 202 and allow induction heating coil 202 and crucible/pan 152 to briefly cool down before the end user removes removable panel 4 from main body assembly 100. As discussed above, the display screen 700 can be used to inform the end user that the material to be vaporized that was inserted into crucible/pan 152 has been completely vaporized.

As discussed above, if the battery 502 needs replaced during a vaporizing session, the end user can easily and quickly hot-swap or replace a used battery 502 for a fully charged battery 502 by simply removing the mouthpiece assembly 300, removing the discharged battery, inserting a charged battery, and re-attaching the mouthpiece assembly 300. As discussed above, the display screen 700 can be used to inform the end user that the battery 502 needs to be replaced.

Once the end user has ended the vaporizing session, the end user can opt to remove the removable panel 4 and empty any unvaporized material or other residue from the crucible/pan 152 into a proper receptacle. It is to be understood that the construction of the crucible/pan 152 and the use of the induction heating coil 202 allow the end user to quickly and easily remove the crucible/pan 152 from the main body assembly 100 in order to proper dispose of the unvaporized material or other residue from the crucible/pan 152.

After the crucible/pan 152 has been emptied of any unvaporized material or other residue from the crucible/pan 152, the crucible/pan 152 can then be placed back onto main body assembly 100, re-loaded with new material to be vaporized, and the removable panel 4 is re-attached to main body assembly 100.

Cleaning of Crucible/Pan

In order to conventionally clean any residue, tar or other material that is not easily removed from crucible/pan 152, the end user can simply use a conventional cleaning substance such as isopropyl alcohol and cotton-tipped swabs. As is known in the vaporizer art, the end user simply applies an amount of the cleaning substance to the cotton-tipped swab. The swab is then used to clean out any hard to remove residue from crucible/pan 152.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper" "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety.

The applicant reserves the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, venous modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the cortex clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein is a new and improved hand-held vaporizer having induction heating. The preferred hand-held vaporizer having induction heating, according to various embodiments of the present invention, offers the following advantages: ease of use; lightness in weight; durability; excellent induction heating characteristics; the ability to prevent unauthorized use of the vaporizer; the use of interchangeable mouthpieces; the use of an external battery; the use of a molecular sensor; portability; and reduced cost. In fact, in many of the preferred embodiments, these advantages of ease of use, lightness in weight, durability, excellent induction heating characteristics, the ability to prevent unauthorized use of the vaporizer, the use of interchangeable mouthpieces, the use of an external battery, the use of a molecular sensor, portability; and reduced cost are optimized to an extent that is considerably higher than heretofore achieved in prior, known hand-held vaporizers.

I claim:

1. A hand-held vaporizer, comprising:
   a removable panel, wherein the removable panel includes
      a plurality of first magnets operatively attached around a periphery of the removable panel; and
   a main body assembly such that the removable panel is removably attached to the main body assembly, wherein the main body assembly includes a plurality of second magnets located around of periphery of the main body assembly such that the plurality of second magnets interact with the plurality of first magnets in order to assist in attaching the removable panel to the main body assembly, and wherein the main body assembly is further comprised of;
   a crucible/pan assembly having a first side and a second side such that a material to be vaporized is located within the first side of the crucible/pan assembly, wherein the crucible/pan assembly is further comprised of:
      a crucible/pan having a plurality of chambers, wherein the crucible/pan is further comprised of a core such that the core is constructed of cast iron, and a layer of titanium diboride ($TiB_2$) that surrounds the core;
      a divider located on the crucible/pan such that the plurality of chambers is divided by the divider;
      an opening located within the divider; and
      an opening located on each of the plurality of chambers,
   an induction heater having a first side and a second side such that the first side of the induction heater is located adjacent to the second side of the crucible/pan assembly for induction heating of the crucible/pan assembly which in turn vaporizes the material to be vaporized located within the first side of the crucible/pan assembly,
   a removable battery assembly located adjacent to the second side of the induction heater,
   an electronics assembly operatively connected to the battery and the induction heater,
   a molecular sensor assembly operatively attached to the electronics assembly for determining a chemical, biological and/or physical composition of the material to be vaporized prior to the material being vaporized; and
   an interchangeable mouthpiece assembly operatively attached to the crucible/pan assembly for allowing vapors from the material to be vaporized to be inhaled by an end user.

2. The hand-held vaporizer, according to claim 1, wherein the removable panel is further comprised of:
   a biometric sensor attached to the removable panel and operatively connected to the electronics assembly; and
   a plurality of locks attached to the removable panel and operatively connected to the biometric sensor.

3. The hand-held vaporizer, according to claim 1, wherein the interchangeable mouthpiece assembly is further comprised of:
   a mouthpiece base having a first end and a second end;
   a mouthpiece operatively attached to the first end of the mouthpiece base;
   at least one mouthpiece magnet operatively connected to the second end of the mouthpiece base for removably attaching the mouthpiece base to the main body assembly; and
   a mouthpiece opening located in the mouthpiece base that operatively connects the mouthpiece to the crucible/pan assembly.

4. The hand-held vaporizer, according to claim 1, wherein the removable battery assembly is further comprised of:
   a battery; and
   an electrical connector operatively connected to the battery and the electronics assembly.

5. The hand-held vaporizer, according to claim 1, wherein the molecular sensor assembly is further comprised of:
   an infrared spectrometer.

6. The hand-held vaporizer, according to claim 1, wherein the hand-held vaporizer is further comprised of:
   a display screen operatively connected to the removable panel.

7. A vaporizer having induction heating, comprising:
   a removable panel, wherein the removable panel includes
      a plurality of first magnets operatively attached around a periphery of the removable panel; and
   a main body assembly such that the removable panel is removably attached to the main body assembly, wherein the main body assembly includes a plurality of second magnets located around of periphery of the main body assembly such that the plurality of second magnets interact with the plurality of first magnets in order to assist in attaching the removable panel to the main body assembly, and wherein the main body assembly is further comprised of;
- a crucible/pan assembly having a first side and a second side such that a material to be vaporized is located within the first side of the crucible/pan assembly, wherein the crucible/pan assembly is further comprised of:
  - a crucible/pan having a plurality of chambers, wherein the crucible/pan is further comprised of a core such that the core is constructed of cast iron, and a layer of titanium diboride (TiB$_2$) that surrounds the core;
  - a divider located on the crucible/pan such that the plurality of chambers is divided by the divider;
  - an opening located within the divider; and
  - an opening located on each of the plurality of chambers,
- an induction heater having a first side and a second side such that the first side of the induction heater is located adjacent to the second side of the crucible/pan assembly for induction heating of the crucible/pan assembly which in turn vaporizes the material to be vaporized located within the first side of the crucible/pan assembly,
- a removable battery assembly located adjacent to the second side of the induction heater,
- an electronics assembly operatively connected to the battery and the induction heater,
- a molecular sensor assembly operatively attached to the electronics assembly for determining a chemical, biological and/or physical composition of the material to be vaporized prior to the material being vaporized, and
- an interchangeable mouthpiece assembly operatively attached to the crucible/pan assembly for allowing vapors from the material to be vaporized to be inhaled by an end user.

8. The vaporizer, according to claim 7, wherein the removable panel is further comprised of:
- a biometric sensor attached to the removable panel and operatively connected to the electronics assembly; and
- a plurality of locks attached to the removable panel and operatively connected to the biometric sensor.

9. The vaporizer, according to claim 7, wherein the interchangeable mouthpiece assembly is further comprised of:
- a mouthpiece base having a first end and a second end;
- a mouthpiece operatively attached to the first end of the mouthpiece base;
- at least one mouthpiece magnet operatively connected to the second end of the mouthpiece base for removably attaching the mouthpiece base to the main body assembly; and
- a mouthpiece opening located in the mouthpiece base that operatively connects the mouthpiece to the crucible/pan assembly.

10. The vaporizer, according to claim 7, wherein the molecular sensor assembly is further comprised of:
an infrared spectrometer.

11. The vaporizer, according to claim 7, wherein the vaporizer is further comprised of:
a display screen operatively connected to the removable panel.

12. A method of using a hand-held vaporizer, comprising the steps of:
- using a molecular sensor located on the main body assembly of the hand-held vaporizer to determine a chemical, biological and/or physical composition of the material to be vaporized prior to the material being vaporized, wherein the main body assembly includes a plurality of first magnets located around of periphery of the main body assembly;
- removing a removable panel from a main body of a hand-held vaporizer, wherein the removable panel includes a plurality of second magnets operatively attached around a periphery of the removable panel;
- inserting a desired amount of a material to be vaporized into a crucible/pan assembly, wherein the crucible/pan assembly is further comprised of:
  - a crucible/pan having a plurality of chambers, wherein the crucible/pan is further comprised of a core such that the core is constructed of cast iron, and a layer of titanium diboride (TiB$_2$) that surrounds the core;
  - a divider located on the crucible/pan such that the plurality of chambers is divided by the divider;
  - an opening located within the divider; and
  - an opening located on each of the plurality of chambers;
- attaching the removable panel back onto the main body assembly of the hand-held vaporizer such that the plurality of first magnets interact with the plurality of second magnets in order to assist in attaching the removable panel to the main body assembly;
- activating an induction heater that is located adjacent to the crucible/pan assembly;
- induction heating the crucible/pan assembly so as to vaporize the material that is to be vaporized;
- transporting a vapor from the vaporized material to an interchangeable mouthpiece assembly; and
- inhaling, by an end user, the vapor from the vaporized material through the interchangeable mouthpiece assembly.

13. The method, according to claim 12, wherein the method is further comprised of the step of:
providing the removable panel with a biometric sensor and a plurality of locks such that the biometric sensor operates in conjunction with the plurality of locks located on the removable panel in order to prevent unauthorized use of the hand-held vaporizer.

14. The method, according to claim 12, wherein the step of using a molecular sensor is further comprised of the step of:
using an infrared spectrometer to determine a chemical, biological and/or physical composition of the material to be vaporized prior to the material being vaporized.

15. The method, according to claim 13, wherein the step of providing the removable panel is further comprised of the step of:
providing a display screen on the removable panel.

* * * * *